(12) United States Patent
Becken et al.

(10) Patent No.: US 7,006,228 B2
(45) Date of Patent: Feb. 28, 2006

(54) METHODS FOR QUANTIFYING THE OXIDATION STATE OF GLASS

(75) Inventors: Keith J. Becken, Avoca, NY (US); David C. Boyd, Somerset, NJ (US); Dorothy E. Sempolinski, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 437 days.

(21) Appl. No.: 10/602,290

(22) Filed: Jun. 24, 2003

(65) Prior Publication Data

US 2004/0263849 A1    Dec. 30, 2004

(51) Int. Cl.
*G01N 21/00* (2006.01)
(52) U.S. Cl. .................................... 356/432
(58) Field of Classification Search ............. 356/432, 356/237; 65/29, 134
See application file for complete search history.

(56) References Cited

U.S. PATENT DOCUMENTS

| | | | |
|---|---|---|---|
| 3,022,181 A * | 2/1962 | Connelly | 501/64 |
| 4,419,118 A | 12/1983 | Reiji et al. | |
| 4,557,743 A | 12/1985 | Claes et al. | |
| 4,975,168 A | 12/1990 | Ohno et al. | |
| 5,776,845 A * | 7/1998 | Boulos et al. | 501/70 |
| 5,824,127 A | 10/1998 | Bange et al. | 65/90 |
| 5,830,812 A * | 11/1998 | Shelestak et al. | 501/71 |
| 6,128,924 A | 10/2000 | Bange et al. | 65/90 |
| 6,195,160 B1 * | 2/2001 | Rainer et al. | 356/135 |
| 6,350,712 B1 | 2/2002 | Cabrera-Ilanos | |
| 6,796,144 B1 * | 9/2004 | Shepard et al. | 65/29.11 |

FOREIGN PATENT DOCUMENTS

JP    2003-137593    5/2003

* cited by examiner

*Primary Examiner*—Layla G. Lauchman
*Assistant Examiner*—Ali Allawi
(74) *Attorney, Agent, or Firm*—Joanne N. Pappas

(57) ABSTRACT

The present invention provides methods for measuring Fe (II) and Fe (III) levels in a glass composition, for using those measured levels for determining a relative oxidation state of the glass material, and for further making a determination based on those measurements as to the quality of the glass material. In addition, methods are presented for determining the reliable quality of ultra fine/ultra thin glass in the time and labor efficient manner.

12 Claims, 3 Drawing Sheets

Example: Extinction Curve with Calculated Curve and Components

METHODS FOR QUANTIFYING THE OXIDATION STATE OF GLASS

BACKGROUND OF THE INVENTION

1. Field of the Invention

The present invention relates generally to methods for measuring iron oxide levels in glass, and particularly to methods for correlating the iron oxide levels in glass with the oxidation state of that glass and further associating the oxidation state of the glass with the quality of the glass.

2. Technical Background

One of the major contributions to the manufacturing costs of glass articles continues to be the presence of defects in end-use glass articles. The presence of these defects in the manufactured glass articles can affect the suitability of the glass article for its application. These defects may be classified as solid in nature (e.g., unmelted raw materials, or other refractory materials) or gaseous in nature (e.g., bubbles or blisters). Chemical constituents are employed in the raw material mixtures to aid in the removal of these latter defects. These constituents are known as fining agents and encompass a range of multivalent oxide and/or halide materials. Typical fining agents are described, for example, in U.S. Pat. No. 5,824,127 (Bange) and U.S. Pat. No. 6,128,924 (Bange).

A relatively new, and demanding, use of glass is as a substrate for Flat Panel Displays (FPDs). One well-known member of this family of displays is the Liquid Crystal Display (LCD). In LCDs, two sheets of glass, each on the order of 1 mm thick, surround a thin, 3–5 $\mu$m, layer of liquid crystal material. Liquid crystal materials encompass a range of organic materials that have the properties of being birefringent (refractive index dependent upon the crystal orientation) and having an ability to switch crystal orientations by the application of an electric field. By applying polarizing films to the outside of this glass-liquid crystal glass "cell", a voltage-controlled valve may be created. Pixelation necessary for a true display is done by applying the necessary voltage to only a small area of the total liquid crystal. This can either be done intrinsically (passive matrix Liquid Crystal Display) or actively through the creation of a thin film transistor (TFT) at each pixel location (Active Matrix Liquid Crystal Display, AMLCD). The addition of an external light source then completes the display.

The optical transmission characteristics of the glass substrate have a direct bearing on the optical performance of these FPDs, and in particular on the AMLCDs. A glass defect on the order of the pixel size may disrupt the optical transmission through that pixel and result in an optical defect in the display that is immediately evident to an observer/user of the display. Increases in both the display size and the display resolution have resulted in increasing demands placed on the glass manufacturer to deliver larger pieces of glass with smaller inclusions. A typical requirement for a glass substrate that will be used in AMLCDs is for the glass to contain no inclusion greater than about 50$\mu$m in an area of glass approximately 1 m×1 m.

To attain such high quality levels in the glass substrate, very tight control must be exercised over the entire glass manufacturing process. To minimize the occurrence of solid inclusions, tight control over the raw materials, melting system, and operation must be maintained. For gaseous inclusions, an additional level of control is incorporated in the manufacturing process, that is, the addition of a particular amount and type of fining agent(s), which is dependent on the efficiency of the fining agent. While a majority of the controls just discussed can be controlled in real time by standard operational controls, the efficiency of the fining agent has proven problematic. For fining packages based on multivalent oxides (e.g., $As_2O_3$, $Sb_2O_3$, $SnO_2$, $CeO_2$, $Fe_2O_3$), the efficiency is tied to the oxides' oxidation state.

The oxidation state of the glass has previously been determined to be reflected in the relative amounts of the iron ions Fe(II) and Fe(III) that exist as tramp components in most manufactured glass. Unfortunately, existing techniques for determining the iron oxidation states in the glass either require expensive and time consuming chemical analysis, for example, Atomic Absorption Spectroscopy (AAS) or Electron Paramagnetic Resonance (EPR) or require less accurate spectrophotographic methods (focused on two wavelengths to monitor a glass property, e.g., 300–400 nm and 1000–1200 nm), which although much quicker are often inconsistent. Therefore, either feedback time is slowed and/or quality of the feedback information is unreliable to the glass technologist or process engineer, making it difficult to make corrective actions within the glass melting process. As a result, there is a need in the industry to be able to accurately follow the iron ion levels, and thereby the oxidation states in the manufactured glass material. This is especially true for glass articles going to the highly demanding FPDs market. There is also a need in the industry for fast, efficient, and accurate methods to avoid producing and shipping unacceptable glass product, and where appropriate, a need to make this determination on site where the glass is manufactured, thereby minimizing the time it takes to make a corrective action. Against this backdrop the present invention has been developed.

SUMMARY OF THE INVENTION

One aspect of the present invention relates generally to the spectroscopic detection of Fe(II) and Fe(III) in glass materials. Detected iron levels provide relative oxidation states of the glass that are consistent with the quality of the glass.

The present invention provides accurate and sensitive methods for measuring Fe(II) and Fe(III) using spectroscopic UV-Vis-spectroscopy. Transmission measurements are converted to extinction coefficients and compared to similar measurements performed on glass samples having known values of Fe(II) and Fe(III). Relative values for Fe(II) and Fe(III) are determined and converted into a relative oxidation state for the glass material. These methods can also be used for measuring and quantifying the levels of other metallic ions within a glass material, for example, manganese, and for further relating these measurements with the quality of the glass. Note that preferred embodiments of the present invention use the whole spectral curve (~350–1400 nm) to measure Fe(II) and Fe(III) levels, thereby improving resolution and sensitivity to measurements made on the glass sample.

Compared to existing chemical analysis methods for measuring iron ion levels or oxidation states in a glass sample, the present invention is less time consuming, less labor intensive, and provides consistent, accurate, and reliable results. These results are often available in a matter of hours as compared to chemical analysis methods, which require days.

In another aspect, the present invention includes a method for determining the quality of a glass material before shipment of the glass material to an end-user. The method includes setting a threshold oxidation state for a glass material, above which the material is not shipped to the end-user. The methods can include providing standardized levels of oxidation states in a glass that correspond to a particular end-use for the glass material. As such, a glass having a particular oxidation state may be best used for a particular end-use, for example use in LCD.

In another aspect of the present invention, the methods include spectroscopically measuring the dissolved water in a glass material to provide an indicator of the glass material quality. The spectroscopically determined dissolved water content of a glass material can be combined with the spectroscopically determined oxidation state of a glass material to provide additional reliability as to the glass material's quality.

In another aspect of the present invention, the methods provide the type and amount of fining agent necessary to optimize the quality of a glass material. In particular, the methods can be used to identify an acceptable fining agent and oxidation state of an acceptable fining agent for use with a particular glass material composition. Other potential parameters that can be optimized in the production of a glass composition, using the methods of the present invention, include temperature changes during glass manufacturing process, nitre concentration added to glass composition during the manufacturing process, and other like parameters.

In another aspect, the methods of the present invention are modified for use in the determination of the oxidation state of ultra pure/ultra fine glass sheets. The methods include steps for accurately measuring the transmission of light through a sample of ultra pure/ultra fine glass and, as above, relating the spectroscopic measurements to a glass sheets' relative quality.

Additional features and advantages of the invention will be set forth in the detailed description that follows and, in part, will be readily apparent to those skilled in the art from that description or recognized by practicing the invention as described herein, including the detailed description that follows the claims, as well as the appended drawings.

It is to be understood that both the foregoing general description and the following detailed description present embodiments of the invention and are intended to provide an overview or framework for understanding the nature and character of the invention as it is claimed. The accompanying drawings are included to provide a further understanding of the invention and are incorporated in and constitute a part of this specification. The drawings illustrate various embodiments of the invention and, together with the description, serve to explain the principles and operations of the invention.

DETAILED DESCRIPTION OF THE PREFERRED EMBODIMENTS

Figure 1:
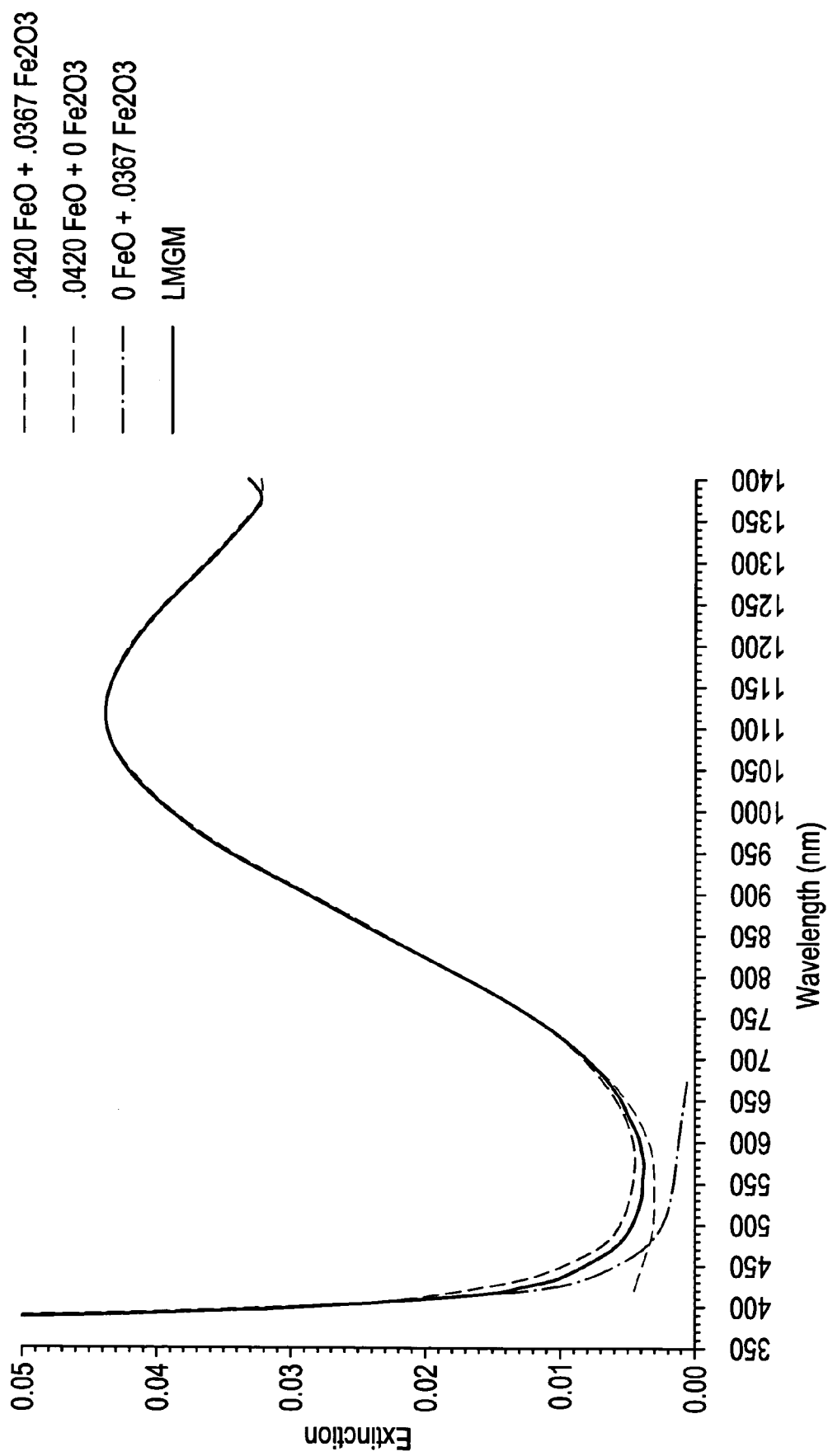
FIG. 1 provides a graphical illustration of the components of the extinction curve in accordance with the present invention.

Reference will now be made in detail to the present preferred embodiments of the invention.

In general, embodiments of the present invention are directed toward providing highly reliable and sensitive methods for measuring the FeO and $Fe_2O_3$ levels in glass material, and in particular within ultra-pure/ultra-fine glass material (typically sheets of glass material), which are useful in LCD and AMLCD devices, among other things. The methods of the invention further provide steps for the conversion of the measured FeO and $Fe_2O_3$ levels in the glass materials to the oxidation state of the same glass material. The methods of the present invention are sensitive, accurate, and relatively quick, compared to non-spectroscopic means, and provide a reliable indicator as to the quality of a particular glass sample, superior in quality to other conventional spectroscopic means.

It should be noted that the methods of the present invention are applicable to most, if not all, types of glass where the partial pressure of oxygen is a concern in the glass's final composition. As noted, the methods of the present invention are most applicable to ultra-pure/ultra-fine glass used in flat panel display devices, where partial pressure of oxygen in the final product has a direct correlation to the number of blisters in the glass. However, it is envisioned that the methods of the present invention are applicable to any glass material that transmits light.

The oxygen concentration, or oxygen partial pressure, in a glass material is strongly correlative to the quality of the particular glass product. For example, a glass material with an unacceptably high partial pressure of oxygen will often exhibit blisters and be non-useable to the end user, i.e., the flat panel display device manufacturer.

In embodiments of the present invention, oxygen levels in a glass material are reflected by the relative amounts of Fe(II) and Fe(III) that exist in the glass material and in particular, by the ratio of Fe(III) to Fe(II) in the glass material. The accurate measurement of iron ion concentrations in a glass is a strong indicator of the oxidation state of the glass and hence the quality of the glass. (See below.) In accordance with the invention, therefore, the present embodiments generally are directed to spectroscopic methods for the sensitive and accurate detection of iron and, hence, oxygen concentration, in a glass material. These methods provide a more cost-effective, convenient, and reliable method for determining the quality of a particular glass material as manufactured for its particular use. The present invention also provides methods for using the measurement of a glass's oxidation state as a tool for optimizing the amount and type of fining agent in a glass material and, further, for optimizing the composition of any target parameter in a glass material.

In accordance with one embodiment of the present invention, a method for measuring oxidation state in a glass material is provided. The method comprises the steps of obtaining a representative sample of glass from a manufactured glass material; measuring the transmission of the glass sample from approximately 200 nm to 3000 nm, and more preferably from 300 nm to 1400 nm, at predetermined wavelength intervals, for example at 10 nm intervals, with a UV-Vis-Spectrophotometer; converting the transmission data into extinction data for each of the measured wavelengths; tabulating each extinction coefficient by wavelength; calculating the iron ion concentrations from the extinction coefficient data; and converting the iron ion concentrations to a relative oxygen partial pressure in the glass sample. The method is based on taking a statistically significant number of readings over a relevant number of wavelengths to provide an accurate series of extinction coefficients.

In accordance with an embodiment of the present invention, a standard curve flow diagram is prepared from a series of glass compositions having known iron ion levels. The standard curve shows a plot where the extinction coefficient is measured for each known iron concentration at a series of relevant wavelengths and then used to determine the iron ion level in glass samples having unknown iron ion levels.

In a first step, a series of test glass compositions are formulated and prepared as is well known in the art. Each test composition, having a known and incrementally varied amount of Fe(II) and Fe(III), for example, 250 ppm, 500 ppm, and 1500 ppm, is prepared. The amount of each iron ion retained in each sample is checked for accuracy using known chemical analysis procedures, for example, total iron can be determined using atomic absorption spectroscopy (AAS). A sample or samples of each glass material, having the predetermined amount of each iron ion, is taken from the glass composition and prepared for transmission experiments. The sample is obtained after the glass composition has cooled and is in a finalized state for end use. In one embodiment, samples of glass for use in the transmission experiments are of a thickness and width to provide accurate transmission of light when an input wavelength of light is received by the sample. In preferred embodiments, the glass sample is from 1 to 2 cm thick, having a diameter of from 1 to 2 inches. The sample can be core-drilled from the glass material and can be polished, preferably to approximately 3 to 10 mm in thickness. It is envisioned that other glass sample dimensions are within the scope of the present invention.

A transmission curve is prepared from each sample having a known iron ion concentration. The range of wavelength of light used in the preparation of the transmission curve is typically from approximately 200 to 3000 nm, and more preferably from 300 to 1400 nm. Measurements are typically taken at every wavelength, and more preferably at 5 nm intervals, and most preferably at 10 nm intervals. Other wavelength intervals can be used, as long as the curve has at least three data points. A broad absorption band at about 1110 nm indicates the presence of Fe(II), whereas the UV cutoff location indicates the amount of Fe(III) present in the sample. See "Optical and EPR Absorption of Iron in Alkaline Earth Aluminosilicate Glasses," P. S. Danielson and J. W. H. Schreurs, Journal of Non-Crystalline Solids, 38 and 39 (1980) 177–182: North-Holland Publishing Company.

The transmission data for each sample is converted to extinction data at each of the measured wavelengths, for example, transmission data between 350 nm to 1400 nm, taken at 10 nm intervals, provides 106 different points of extinction data. Conversion of transmission data to extinction data is well known in the art. Briefly, the formula $T(\lambda)=100(1-R)^2 e^{-e(\lambda)t}$ (formula 1) is used, where the quantity $100(1-R)^2$ is 91.59 (Reference index equals 1.523). Extinction coefficients ($\epsilon_\lambda$) are approximated as linear functions of the weight percents of the iron ions so that the $\epsilon_\lambda$=linear function of iron ions=$m_{2\lambda}$*Fe(II)+$m_{3\lambda}$*Fe(III) (formula 2). Using the known values of iron in each glass composition, a calculated extinction coefficient is determined for each wavelength by taking the sum of the values times the appropriate coefficients (see Examples below for more detail) That calculated extinction coefficient is then used to calculate a standardized transmission curve between the tested wavelengths, for example 350 nm to 1400 nm.

The steps listed above can be extended to determine an unknown value of iron ion from a sample's transmission data. A sample is taken from a glass composition having an unknown value of iron ion, for example, a sample from a batch of glass material to be used in a display device. As above, the sample is of a sufficient thickness and width to support accurate transmission data. A transmission curve is measured for a range of wavelengths, for example, from 350 nm to 1400 nm, and converted to an extinction curve, using formula 1 above. Each measured extinction coefficient is tabulated by wavelength. The data from one or more standardized, i.e., known iron ion concentration curves, is then subtracted from the measured curve for the unknown iron ion concentration curve. The difference between the two curves provides a "residual value." The residual values are squared and then summed to a single number called the "sum of the squares." Successive iterations are then performed on the data to find the Fe(II) and Fe(III) values that give a "minimum sum of the squares". This last step is typically performed by a program that does successive iterations toward a numerical goal, for example, the Solver program in Excel or other like programs. As such, the values of iron ion concentration for a glass material are developed from the transmission data from that sample.

A graphical illustration of the components of the extinction curve and the above procedure is shown in FIG. 1. The solid line is the measured extinction curve for a sample having a known value for Fe(II) and Fe(III). The short-dashed line is the calculated extinction curve from the Fe(II) and Fe(III), calculated from the Solver program. The other two curves are the two components of the broken line that result from the input of the Fe(II) and Fe(III) values. The gap between the broken line and solid line provides the residual values.

In a preferred embodiment of the present invention, the glass material having an unknown value of Fe(II) and Fe(III) is ultra fine/ultra pure glass, for example, Corning incorporated code 1737 and Eagle 2000™ glass. Since ultra fine/ultra pure glass is manufactured in thin sheets, typically not sufficient in thickness to obtain transmission data, a sample must be prepared for optical transmission study. Manufactured sheets of ultra fine/ultra pure glass are scored into approximate 1 inch by 1 inch squares. Each square is cleaned using a solution of detergent in DI water, followed by rinsing and air drying. The cleaning takes place in a class 1000 clean room. The cleaned 1 inch by 1 inch glass squares are stacked into approximate 1 cm thick stacks (approximately 14 sheets stacked, where each sheet is approximately 0.7 mm thick). Each stack is held together using a clamp. The edges of the stack should form a flat edge or side for receiving the input light during the transmission testing. This procedure ensures that the glass sheets are in optical contact with one another and thereby minimizes light scattering when measured with the UV-Vis-spectrophotometer. In this manner, the iron ion concentrations in ultra pure/ultra fine glass can be determined by simply measuring the transmission of the glass over a range of relevant wavelengths and performing the steps as described above. This is of particular importance where the iron level measurements can be made immediately following production of the glass, in preparation of the glass for shipment to an end-user, for example, a manufacturer of LCDs.

The above methods can also be used to determine the amounts of other metallic ions in a glass material. For example, the above methods can be used to determine the concentrations of manganese in a sample, where an absorption peak develops around 430 nm that increases as concentration of manganese increases.

The spectroscopically measured iron ion concentrations, or other metallic ion concentrations, for an unknown glass material sample, can be converted to relative partial pressure of oxygen, using the following thermodynamic considerations. In general, a measure of relative oxygen concentration from iron levels in a glass material, can be calculated by using the equilibrium constant of the following equation:

$$2Fe_2O_3 = 4FeO + O_2 \quad \text{(formula 3)}$$

$$Keq = [FeO]^4 * [O_2]/[Fe_2O_3]^2 \quad \text{(formula 4)}$$

Inserting a typical temperature used during the production of glass, 1400° C., the equilibrium constant reduces to $5.51 \times 10^{-6}$. In this way the above equation can be solved for the oxygen partial pressure as follows:

$$pO_2 = Keq * [Fe_2O_3]^2/[FeO]^4 \quad \text{(formula 5)}$$

$$\log(pO_2) = \log(Keq) + \log([Fe_2O_3]^2/[FeO]^4) \quad \text{(formula 6)}$$

$$\log(pO_2) = \log([Fe_2O_3]^2/[FeO]^4) - 5.26 \quad \text{(formula 7)}$$

Note that for purposes of this embodiment, iron oxide "concentration" is used in formula 7 rather than iron oxide "activity." Since the iron oxide in glass material likely follows Henry's Law, the molar concentrations are related to activity by Henrian activity coefficients. As such, formula 7 represents an approximation of the iron oxide activities and not the actual concentrations.

As such, in one embodiment of the present invention, the relative partial pressure of oxygen in a glass sample is determined by inserting the spectroscopically measured molar concentrations of the two iron oxides into formula 7. This is not meant to provide an exact figure, but rather to provide a relative gage on whether a sample, in relation to other production type glass materials and to standardized samples having known levels of oxygen, has an acceptable level of oxygen for a glass materials end use. This is determined to some extent empirically, where the quality of glass, i.e., the number of blisters in the glass, is initially determined using standard quality control methods for blister count and related to the relative partial pressure of oxygen as determined using the methods of the present invention.

Finally, the relative partial pressure of oxygen can be spectroscopically followed, using the above methods, as parameters in the glass composition are changed or modified, thereby indicating whether the changed parameter had a positive or negative effect on the oxygen level in the glass material. For example, the effectiveness of different types and oxidation states of fining agents can be followed as to their ability to reduce or scavenge the oxygen in the glass material. In one embodiment, the effectiveness of antimony or arsenic as a fining agent can be followed and optimized by varying the amount, oxidation state, and timing of the addition. In another embodiment, the effect of melting temperature on the partial pressure of oxygen in the glass is followed using the spectroscopic methods of the present invention. The ability to follow individual parameters relevant to manufacturing a glass composition allows both quality and cost to be optimized in the final glass material product for an end-use.

Finally, Infrared (IR) transmission curves can be prepared to determine the dissolved water content of a glass material either independently or at the same time as the iron ion levels are spectromically determined. The measurement of the dissolved water content in a sample provides an independent indicator of the relative oxygen level in the target glass material (the greater the amount of dissolved water, the greater the amount of available oxygen for release as bubbles into the glass material).

Dissolved water in a glass material has an absorption region of approximately 3800–3100 cm$^{-1}$. The relative linear hydroxyl concentration coefficient ($\beta_{OH}$) is calculated on a glass sample using the following equation:

$$\beta_{OH} = x^{-1} \log(T_{3845}/T_{3570}) \quad \text{(formula 8)}$$

where $T_{3845}$ refers to the transmission at 3845 cm$^{-1}$ (non-OH absorbing region) and $T_{3570}$ refers to the transmission at 3570 cm$^{-1}$ (OH-peak transmission) at a sample thickness of x mm.

The dissolved water determination can be performed in conjunction with, or independent of, the iron ion concentration determinations as described in other embodiments of the present invention. The dissolved water determination provides a second indicator of a glass material's possible quality. In some embodiments a matrix of glass quality is prepared using the glass compositions' $O_2$ levels and water levels as quality indicators.

EXAMPLES

The invention will be further clarified by the following examples, which are provided by way of illustration and are not intended as limiting.

Example 1

Preparation of Experimental Glass Melts Having Known Compositions

Experimental Design: A series of experimental glass melts were formulated having known quantities of several test variables. Boroaluminosilicate glass, the glass used in most AMLCD devices, was used as a substrate for the addition of each of the independent test variables. Two base boroaluminosilicate glass types were used in the experiment, Corning code 1737, and Corning Code Eagle$^{2000™}$. Glass was fined with either arsenic (F) or antimony (G) as is well known in the art. Test variables included the following:
  MnO (0, 0.5, or 1.0 weight % expressed as MnO$_2$);
  FeO (250, 750, or 1500 parts per million (PPM)) by weight expressed as Fe$_2$O$_3$;
  Glass Type (Corning Code 1737F, 1737G, Eagle$^{2000™}$F, or Eagle$^{2000™}$G);
  Oxidation State (low (carbon), medium (nothing), high (nitrate—Ba, Sr or NH$_4$) (0 or 2 weight % expressed as NO$_2$)).

Sixty-three melts in randomized, factorial design, with replicates, were prepared to study the Code 1737 F and G based glasses and eighteen melts were used to study the Eagle$^{2000™}$F and G based glasses. Each glass melt is coded as shown in Table 1 using the following code:
  First letter (L, M, H) means low, medium, or high MnO$_2$;
  second letter (L, M, H) means low, medium, or high Fe$_2$O$_3$;
  third letter means glass type: "F" glass means arsenic fined and "G" glass means antimony fined for Code 1737 glass, or "A" means As$_2$O$_3$ and "S" means Sb$_2$O$_3$ for Eagle$^{2000™}$ glass;
  fourth letter (L, M, H) means low, medium, or high oxidation (carbon, nothing, or nitre).

Glass Melt Preparation: Each experimental glass melt formulation was melted for six hours at 1650° C. in 500 cc platinum crucibles and stirred with a Vycor® brand glass rod to avoid cross contamination. Each glass melt was "optically" poured into >1 cm thick patties and annealed at 725°

C. Patties were cooled overnight in the annealer. Four 1.5 inch diameter discs were core-drilled from each patty, two were polished to 10 mm thickness, and two were polished to 3 mm thickness.

Each glass patty was chemically analyzed for total iron using Atomic Absorption Spectroscopy (AAS), total manganese using AAS, and $As_2O_3$ and $Sb_2O_3$ using two forms of plasma spectroscopy, ICP and DCP. The iron oxidation states, $Fe(+3)_2O_3$ and $Fe(+2)O$, were determined using Electron Paramagnetic Resonance (EPR) (Fe(+3)) and colorimetry (Fe(+2)). Note that iron oxidation states were only analyzed on the glass patties without manganese added, i.e., 20 of the 1737 series and 18 of the Eagle[2000]™ series.

Results: These results illustrate that a series of eighty-one experimental glass melts were prepared for further testing having known, i.e., measured, values for total iron, manganese, $As_2O_3$, and $Sb_2O_3$. Transmission measurements were then performed on each. These experimental glass melts were then analyzed using a UV-Vis-NIR Spectrophotometer to obtain each glass melts transmission measurements.

TABLE 1

Iron Oxide Concentrations Calculated From Model And Measured By Chemical Analysis For Experimental Melts

| | | Calculated With Model | | Chemical Analysis | |
|---|---|---|---|---|---|
| Glass # | Glass ID | FeO, wt % | $Fe_2O_3$, wt % | FeO, wt % | $Fe_2O_3$, wt % |
| 1 | LLFL | 0.008 | 0.019 | 0.009 | 0.017 |
| 2 | LLGH | 0.015 | 0.009 | 0.015 | 0.009 |
| 3 | LMFM | 0.025 | 0.058 | 0.028 | 0.053 |
| 4 | MMFH | 0.023 | 0.068 | | |
| 5 | MMGL | 0.060 | 0.007 | | |
| 6 | HLGM | 0.015 | 0.015 | | |
| 7 | HMGM | 0.044 | 0.041 | | |
| 8 | HHFL | 0.052 | 0.146 | | |
| 9 | HHGH | 0.074 | 0.109 | | |
| 10 | LMGM | 0.042 | 0.037 | 0.039 | 0.032 |
| 11 | LHGH | 0.043 | 0.129 | 0.052 | 0.111 |
| 12 | LHGL | 0.126 | 0.013 | 0.120 | 0.008 |
| 13 | MLFH | 0.008 | 0.027 | | |
| 14 | MMGL | 0.019 | 0.072 | | |
| 15 | MMGH | 0.035 | 0.053 | | |
| 16 | HLFH | 0.008 | 0.030 | | |
| 17 | HLGL | 0.027 | 0.019 | | |
| 18 | HMFM | 0.023 | 0.082 | | |
| 19 | LLGL | 0.023 | 0.010 | 0.020 | 0.002 |
| 20 | LMGL | 0.059 | 0.006 | 0.061 | 0.007 |
| 21 | LHFL | 0.053 | 0.106 | 0.059 | 0.095 |
| 22 | LHGH | 0.076 | 0.081 | 0.086 | 0.071 |
| 23 | MMFM | 0.028 | 0.069 | | |
| 24 | MMGM | 0.045 | 0.036 | | |
| 25 | HLFL | 0.010 | 0.026 | | |
| 26 | HLGH | 0.015 | 0.017 | | |
| 27 | HMGL | 0.063 | 0.007 | | |
| 28 | LLFH | 0.009 | 0.021 | 0.009 | 0.018 |
| 29 | LMFM | 0.025 | 0.058 | 0.025 | 0.046 |
| 30 | LMFH | 0.038 | 0.040 | 0.029 | 0.051 |
| 31 | LMGH | 0.038 | 0.040 | 0.037 | 0.033 |
| 32 | MLGL | 0.021 | 0.005 | | |
| 33 | MMFL | 0.026 | 0.064 | | |
| 34 | HMFH | 0.024 | 0.081 | | |
| 35 | HHFH | 0.048 | 0.140 | | |
| 36 | HHGL | 0.119 | 0.012 | | |
| 37 | LMFL | 0.026 | 0.058 | 0.025 | 0.051 |
| 38 | MLFM | 0.008 | 0.025 | | |
| 39 | MLGM | 0.015 | 0.012 | | |
| 40 | MMGH | 0.039 | 0.043 | | |
| 41 | MHFM | 0.053 | 0.130 | | |
| 42 | MHGM | 0.091 | 0.067 | | |
| 43 | HMFL | 0.024 | 0.074 | | |
| 44 | HMGH | 0.039 | 0.051 | | |
| 45 | HHFM | 0.050 | 0.155 | | |
| 46 | LLFM | 0.008 | 0.019 | 0.008 | 0.018 |
| 47 | LLGL | 0.020 | 0.004 | 0.019 | 0.000 |

TABLE 1-continued

Iron Oxide Concentrations Calculated From Model And Measured By Chemical Analysis For Experimental Melts

| | | Calculated With Model | | Chemical Analysis | |
|---|---|---|---|---|---|
| Glass # | Glass ID | FeO, wt % | $Fe_2O_3$, wt % | FeO, wt % | $Fe_2O_3$, wt % |
| 48 | LLGM | 0.015 | 0.010 | 0.015 | 0.007 |
| 49 | MLFL | 0.008 | 0.023 | | |
| 50 | MLGH | 0.014 | 0.013 | | |
| 51 | MHFL | 0.051 | 0.121 | | |
| 52 | MHGH | 0.076 | 0.092 | | |
| 53 | HHFM | 0.047 | 0.145 | | |
| 54 | HHGM | 0.091 | 0.075 | | |
| 55 | LHFM | 0.044 | 0.111 | 0.046 | 0.104 |
| 56 | LHGM | 0.087 | 0.063 | 0.082 | 0.050 |
| 57 | MLFH | 0.008 | 0.025 | | |
| 58 | MLGL | 0.028 | 0.024 | | |
| 59 | MHFH | 0.045 | 0.157 | | |
| 60 | MHGL | 0.122 | 0.013 | | |
| 61 | HLFM | 0.008 | 0.029 | | |
| 62 | HLGM | 0.014 | 0.016 | | |
| 63 | HHFL | 0.045 | 0.144 | | |
| 64 | LLAL | 0.009 | 0.017 | 0.012 | 0.014 |
| 65 | LMSL | 0.045 | 0.012 | 0.053 | 0.015 |
| 66 | LHAL | 0.060 | 0.115 | 0.063 | 0.073 |
| 67 | LLSM | 0.012 | 0.010 | 0.012 | 0.010 |
| 68 | LMAM | 0.030 | 0.055 | 0.032 | 0.045 |
| 69 | LHSM | 0.080 | 0.049 | 0.087 | 0.044 |
| 70 | LLAH | 0.008 | 0.021 | 0.011 | 0.015 |
| 71 | LMSH | 0.032 | 0.039 | 0.035 | 0.036 |
| 72 | LHAH | 0.061 | 0.111 | 0.076 | 0.067 |
| 73 | LLSL | 0.016 | 0.003 | 0.014 | 0.004 |
| 74 | LMAL | 0.026 | 0.043 | 0.036 | 0.036 |
| 75 | LHSL | 0.091 | 0.015 | 0.110 | 0.019 |
| 76 | LLAM | 0.008 | 0.017 | 0.011 | 0.014 |
| 77 | LMSM | 0.038 | 0.029 | 0.046 | 0.033 |
| 78 | LHAM | 0.063 | 0.123 | 0.062 | 0.073 |
| 79 | LLSH | 0.011 | 0.012 | 0.012 | 0.012 |
| 80 | LMAH | 0.028 | 0.052 | 0.033 | 0.042 |
| 81 | LHSH | 0.064 | 0.086 | 0.067 | 0.073 |

Example 2

Transmission Data from Experimental Glass Melts Provides Accurate Total Iron and Manganese Levels Experimental Design: The series of experimental glass samples discussed in Example 1 were used to correlate total iron levels in each glass sample with the sample's transmission curve. That data was then used to develop a model used for calculating the FeO and $Fe_2O_3$ levels in Corning Incorporated code 1737 and Eagle[2000]™ glasses.

Transmission Measurements: Transmission measurements of the experimental glass melts were performed using the 3 mm thick and 10 mm thick polished discs (from the two discs at each thickness, the one containing the least amount of striae and seeds was selected and used for the measurement). Transmission curves from 200 nm to 1400 nm were obtained using the 10 mm thick discs, with a UV-Vis-NIR Spectrophotometer. A broad absorption band at about 1110 nm indicates the presence of Fe(+2) and the UV cutoff location indicates the amount of Fe(+3) present within each glass sample. For glass samples containing manganese, an absorption peak at about 430 nm develops that increases with manganese concentration.

The 3 mm thick polished discs were used to obtain infrared (IR) transmission curves, including the dissolved water absorption region (3800–3100 cm$^{-1}$), using a Fourier Transform Infrared Spectrometer (FTIR). Relative linear hydroxyl concentration coefficient (a.k.a. $\beta_{OH}$) was calculated for each glass sample using the following equation:

$$\beta_{OH} = x^{-1} \log(T_{3845}/T_{3570})$$

where $T_{3845}$ refers to the transmission at 3845 cm-1 (non-OH absorbing region) and $T_{3570}$ refers to the transmission at 3570 cm-1 (OH-peak transmission) at a sample thickness of x mm.

Note that transmission measurements were also performed on a series of low iron containing production glasses using a UV-VIS-NIR spectrophotometer. These samples, production melted sheet glass, were cleaned and one-inch square, 0.7 mm thick, glass sheets were stacked and measured by edge illumination, as a means for increasing the path length to obtain measurable Fe(II) and Fe(III) absorption (see below).

Transmission data obtained from the above detailed methods was converted to extinction data at 106 different wavelengths (10 nm intervals for wavelengths between 350 nm and 1400 nm) for each sample. The formula used was:

$$T(\lambda) = 100(1-R)^2 e^{-e(\lambda)t}$$

where the quantity $100(1-R)^2$ is 91.59 (Ref index=1.523). Data is plotted as extinction curves.

The extinction coefficient ($\epsilon_\lambda$) is assumed to be a linear function of the weight percents of the colorant ions, i.e., $\epsilon_\lambda$=linear function of colorants=$m_{2\lambda}$*Fe(II)+$m_{3\lambda}$*Fe(III). As such, every tested glass has 106 extinction coefficients, and twenty of the glass samples have also been analyzed for Fe(III) and Fe(II) values. Therefore, 106 sets of regression coefficients, $m_{2\lambda}$ and $m_{3\lambda}$, were calculated by 106 different multiple regression analysis. Each regression had 20 observations (20 sets of Fe(II) and Fe(III) values) for support. The sum of the Fe(II) and Fe(III) values times the appropriate coefficients gives the calculated extinction coefficient for each wavelength ($\epsilon_\lambda$ equation above). The extinction coefficient can then be used to calculate the transmission curve between 350 nm and 1400 nm at 10 nm intervals.

Model For Calculating Iron Values From Transmission Data. Measured transmission curves are converted to extinction curves. The measured extinction coefficients are tabulated by wavelength. A trial extinction curve is calculated using nominal values for Fe(II) and Fe(III). The trial extinction curve is subtracted from the measured curve. The difference between the measured and trial curve is termed the "residuals." The residuals are squared and then summed to a single number termed the "sum of the squares." Using "Solver" in Excel, or other like software, successive iterations are made toward Fe(II) and Fe(III) values that give the minimum "sum of the squares" result.

Figure 2:
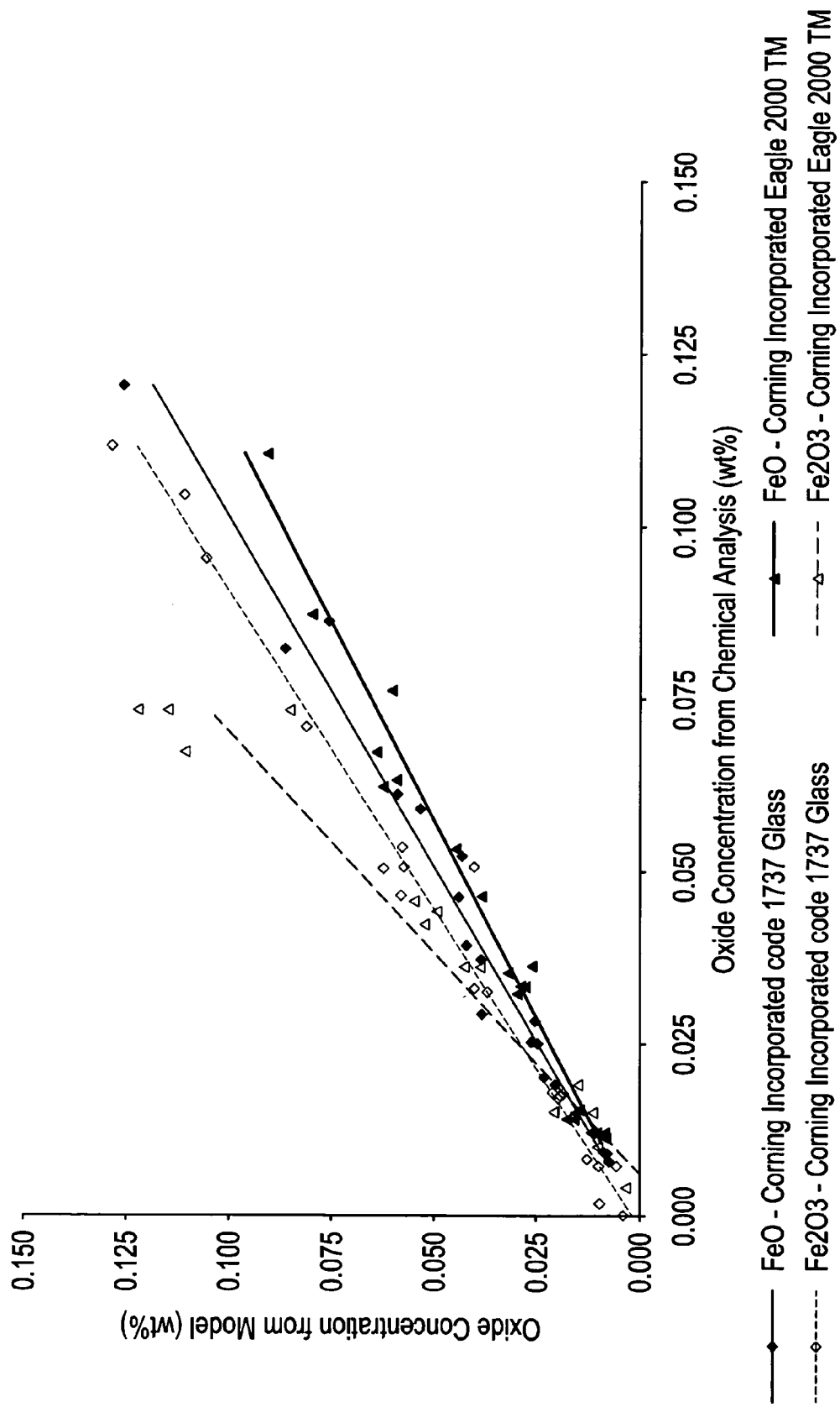
FIG. 2 provides a graphical representation of the reliability of using the embodiments of the present invention for several glass samples, compared to actual measurements on the samples using chemical analysis, for Fe(II) and Fe(III).

Results: Referring to FIG. 1, a graphical illustration of the components of the extinction curves is provided. The solid line is the measured extinction curve for one of the experimental glass samples (LMGM). The short-dashed line shows the calculated extinction curve from the Fe(II) and Fe(III) values resultant from Solver. The other two extinction curves are the two components of the dotted line that result from the input of the Fe(II) and Fe(III) values. The gap between the dotted line and the solid line represents the residual. This data illustrates how closely the model for calculating iron values from transmission data comes. FIG. 2 further illustrate how closely the model comes to predicting the iron ion concentration in the experimental glass samples. Note that the calculated values from Solver are plotted against the measured value for each experimental glass sample. Note that measured values are by colorimetry for Fe(II), EPR for Fe(III), and AAS for $Fe_2O_3$ (total iron). The total iron from Solver is the sum of the Fe(II) and Fe(III), each expressed as $Fe_2O_3$.

Example 3

A Glass Sample's Iron Oxide Ratio is an Indicator of that Sample's Oxygen Partial Pressure Experimental Design: The iron ion concentrations as determined in Example 2 can be converted to a ratio of FeO and $Fe_2O_3$ concentrations (mole fraction) and used as an indicator of oxygen levels in a glass sample.

Equilibrium constants: A measure of oxygen is calculated by using the appropriate equilibrium constant of the following equation:

$$2Fe_2O_3 = 4FeO + O_2$$

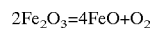

$$Keq = [FeO]^4 * [O_2]/[Fe_2O_3]^2$$

1400° C. was chosen as a somewhat arbitrary but relevant temperature for use in determining a value for the equilibrium constant:

$$Keq = 5.51 \times 10^{-6} (1400° C.)$$

As such, solving for the oxygen partial pressure and taking the log of both sides gives:

$$PO_2 = (Keq) * [Fe_2O_3]^2/[FeO]^4$$

$$\text{Log}(PO_2) = \text{Log}[Keq] + \text{Log}([Fe_2O_3]^2/[FeO]^4) = \text{Log}([Fe_2O_3]^2/[FeO]^4) - 5.26$$

Thus, a measure of the oxygen partial pressure for any glass sample is obtained by substituting into the last equation the molar concentrations of the two oxides of iron. It is recognized that equilibrium equations use activities of the reactants, not their "concentrations." In concentrated solutions, which obey Rauolt's law (that the activity is equal to the concentration), the mole fraction is a good measure of activity. However, dilute solutions more likely obey Henry's law (that the activity is proportional to the concentration). In Henrian solutions, the activity is related to the molar concentration by a constant, the Henrian activity coefficient. As such, the above equation approximates the activities by using the molar concentrations, but does not provide an exact partial pressure of oxygen. These approximations provide an understanding of the change in oxygen partial pressure with changes in iron oxide concentrations.

Note also that the ratio of iron oxide concentrations can also be used as an indicator of +5/+3 ratio of a fining agent in a glass sample. For example:

$$2Fe_2O_3 = 4FeO + O_2$$

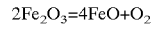

$$Keq = [FeO]^4 * [O_2]/[Fe_2O_3]^2 = 5.51 \times 10^{-6} \text{ at } 1400° C.$$

And considering antimony and arsenic equations:

$$Sb_2O_3 + O_2 = Sb_2O_5$$

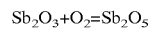

$$Keq = [Sb_2O_5]/([Sb_2O_3]*[O_2]) = 6.36 \times 10-6 \text{ at } 1400° C.$$

$$As_2O_3 + O_2 = As_2O_5$$

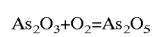

$$Keq = [As_2O_5]/([As_2O_3]*[O_2]) = 9.58 \times 10-5 \text{ at } 1400° C.$$

Combining either of these last equilibria with the iron equilibria gives:

$$[Sb_2O_5]/[Sb_2O_3]=(6.36\times10^{-6})*(5.51*10^{-6})x[Fe_2O_3]^2/[FeO]^4$$

$$[Sb_2O_5]/[Sb_2O_3]=3.5\times10^{-11}x[Fe_2O_3]^2/[FeO]^4$$

$$[As_2O_5]/[As_2O_3]=53\times10^{-11}x[Fe_2O_3]^2/[FeO]^4$$

Experimental and production glasses from Example 1 or 2 (10 mm thick polished discs for experimental glasses and 0.7 mm thick, one inch-by-one inch squares, for production glass) were measured for iron concentrations as discussed in Example 2 and data converted to FeO and $Fe_2O_3$ concentrations (molar ppm), as above.

Figure 3:
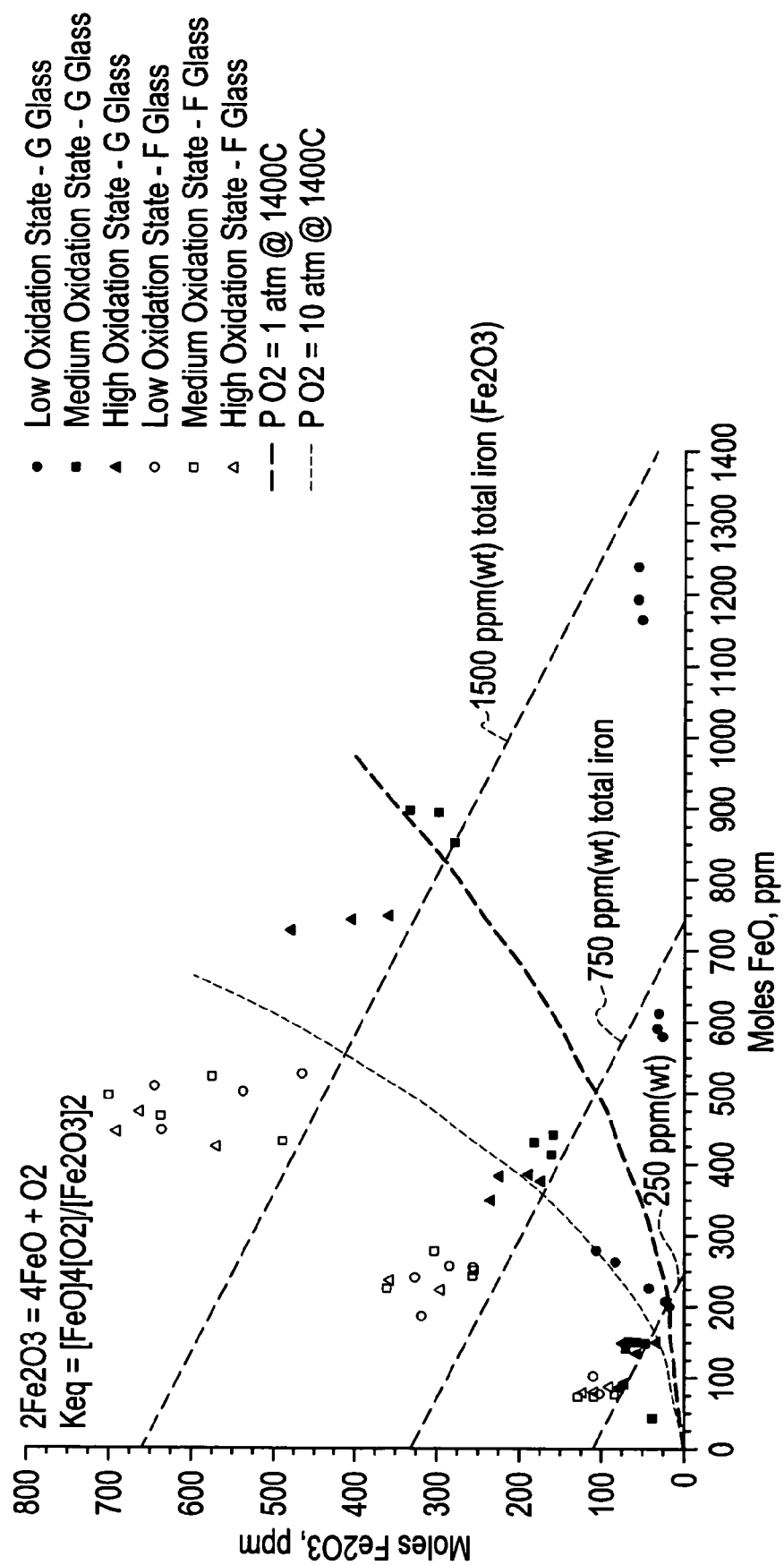
FIG. 3 provides a plot of moles of $Fe_2O_3$ against FeO. Note that samples had varying concentrations of iron (250, 750 and 1500 ppm total $Fe_2O_3$).

Results: FIG. 3 provides a plot of moles of $Fe_2O_3$ against FeO, where each tested glass sample is placed on the graph according to the sample's $Fe_2O_3$ and FeO concentrations. Grid lines on the graph represent total $Fe_2O_3$ (ppm by weight). Each grid line runs from the upper left to the lower right. Note that the experimental glasses were designed to vary greatly in total iron.

A second set of gridlines (oxygen isobars) is the set of two curved lines running more or less perpendicular to the total iron lines, from the origin up and to the right. These gridlines depict the calculated change in oxygen partial pressure as the $FeO/Fe_2O_3$ ratio changes. The oxygen isobar gridlines provide an understanding that a shift in the $FeO/Fe_2O_3$ ratio changes the oxygen partial pressure, and that the change can be substantial, for example an order of magnitude. Therefore, placement on the graph indicates both total iron content (increasing from lower left to upper right) and relative oxidation state (increasing oxidation in the upper left and more reduced in the lower right).

Trends From FIG. 3: FIG. 3 indicates the following:
(1). Most of the antimony fined "G" glasses are to the lower oxygen partial pressure side of the 1 atmosphere isobar, and most of the arsenic fined "F" glasses are in the higher oxygen region.
(2). Arsenic appears to dominate the oxidation state of the glass samples whereas the antimony has a much smaller effect.
(3). The ratio of FeO to $Fe_2O_3$ can be modified by changing the experimental conditions of the glass.

Example 4

Oxygen Levels of Production Glass can be Specroscopically Followed

Experimental Design:

Glass compositions were prepared and formed into thin sheets of ultra fine/ultra pure glass having production glass dimensions. Sheets were scored into 1 inch by 1 inch squares, cleaned, and stacked into 1 cm thick stacks (approximately 14 sheets). Stacks were held together using a clamp. Spectroscopic measurements and calculations were similar to those illustrated in Examples 1–3.

Results:

The data illustrate that consistent and useful data is obtained using the methods of the present invention, again indicating the utility of the present invention with regard to production type glass. The approach is valid whether measurements are done on bulk glass or thin sheets. Also, it can be seen that the model is effective over a large range of iron concentrations.

It will be apparent to those skilled in the art that various modifications and variations can be made to the present invention without departing from the spirit and scope of the invention. Thus it is intended that the present invention cover the modifications and variations of this invention provided they come within the scope of the appended claims and their equivalents.

What is claimed is:

1. A method for determining the partial pressure of oxygen in a glass material comprising:
    measuring the optical transmission of the glass material using a plurality of wavelengths of light appropriate for detecting FeO and $Fe_2O_3$ content;
    converting each measured optical transmission performed on the glass material to an extinction coefficient; and
    converting the entirety of the extinction coefficient data to a ratio of $[Fe_2O_3]^2/[FeO]^4$ content in the glass material, wherein the ratio of $[Fe_2O_3]^2/[FeO]^4$ is proportional to the partial pressure of oxygen in the glass material.

2. The method of claim 1, wherein the measuring of the optical transmission of the glass material is at three or more intervals between wavelengths of approximately 350 nm and 1400 nm.

3. The method of claim 1, wherein the measuring of the optical transmission of the glass material is at 10 nm intervals between the wavelengths of approximately 350 nm and 1400 nm.

4. The method of claim 1, wherein the glass material is ultra-pure/ultra-fine glass material and the method further comprises stacking a plurality of thin sheets of the ultra-pure/ultra-fine glass material to form an edge for measuring the optical transmission.

5. The method of claim 4, wherein the edge is approximately 1 cm thick.

6. A method for quantifying a change in operating conditions for the production of a glass material comprising:
    preparing a first glass material using a first set of operating conditions;
    spectroscopically determining the ratio of $[Fe_2O_3]^2/[FeO]^4$ in the first glass material using a plurality of wavelengths between 350 nm and 1400 nm;
    converting the ratio of $[Fe_2O_3]^2/[FeO]^4$ into a relative partial pressure of oxygen in the first glass material;
    preparing a second glass material using a second set of operating conditions;
    spectroscopically determining the ratio of $[Fe_2O_3]^2/[FeO]^4$ in the second glass material using a plurality of wavelengths between 350 nm and 1400 nm;
    converting the ratio of $[Fe_2O_3]^2/[FeO]^4$ into a relative partial pressure of oxygen in the second glass material; and
    comparing the partial pressure of oxygen in the first glass material to the partial pressure of oxygen in the second glass material, wherein the comparison provides direction for making a change to the first or second operating conditions.

7. The method of claim 6, wherein the operating conditions comprise addition of a fining agent.

8. A method for measuring an oxidation state in an ultra-pure/ultra-fine sheet of production glass comprising:
    preparing a plurality of production glass samples from the production glass;
    stacking the plurality of production glass samples to provide at least one cut edge of the stack;

measuring the optical transmission of the stacked production glass samples by shining a wavelength of light appropriate for detecting FeO and $Fe_2O_3$ content through the cut edge of the stack;

converting each measured optical transmission performed on the production glass to an extinction coefficient; and converting the entirety of the extinction coefficient data to a ratio of $[Fe_2O_3]^2/[FeO]^4$ content in the production glass material, wherein the ratio of $[Fe_2O_3]^2/[FeO]^4$ is proportional to the oxidation state in the ultra-pure/ultra-fine sheet of production glass.

9. The method of claim 8, wherein the at least one cut edge of the stack is approximately 1 cm thick.

10. The method of claim 9, wherein the cut edge is substantially flat.

11. The method of claim 8, wherein the optical transmission of at least one of the stacked production glass samples is measured at 10 nm intervals between the wavelengths of approximately 350 nm and 1400 nm.

12. A method for assigning a glass material to an appropriate use based on the partial pressure of oxygen in the glass material, the method comprising:

measuring optical transmission of the glass material using three or more wavelengths of light between 200 nm and 3000 nm;

converting each measured optical transmission performed on the glass material to an extinction coefficient;

converting the entirety of the extinction coefficient data to a ratio of $[Fe_2O_3]^2/[FeO]^4$ content in the glass material, wherein the ratio of $[Fe_2O_3]^2/[FeO]^4$ is proportional to the partial pressure of oxygen in the glass material; and assigning the glass material, based on its partial pressure of oxygen, to a use, wherein each use can only be provided glass materials having an associated upper threshold level of oxygen.

\* \* \* \* \*